United States Patent [19]

Ziemelis et al.

[11] Patent Number: 4,597,964

[45] Date of Patent: Jul. 1, 1986

[54] CATIONIC POLYDIORGANOSILOXANES FOR TREATING PROTEINACEOUS SUBSTRATES

[75] Inventors: Maris J. Ziemelis; Charles A. Roth, both of Midland, Mich.

[73] Assignees: Aplin & Barrett, Ltd., Dorset, England; Dow Corning Corporation, Midland, Mich.

[21] Appl. No.: 615,422

[22] Filed: May 30, 1984

Related U.S. Application Data

[62] Division of Ser. No. 561,404, Dec. 14, 1983, Pat. No. 4,472,566.

[51] Int. Cl.$^4$ .......................... A61K 7/06; A61K 7/09; A61K 7/11; A61K 7/15
[52] U.S. Cl. ........................................ 424/70; 424/59; 424/60; 424/63; 424/65; 424/66; 424/68; 424/71; 424/72; 424/73; 427/387; 427/389; 428/447; 514/844; 514/845; 514/846; 514/847
[58] Field of Search .................. 424/70; 427/387, 389; 428/447

[56] References Cited

U.S. PATENT DOCUMENTS 3,208,911 9/1965 Oppliger et al. ...................... 424/70
3,278,455 10/1966 Twitchett ............................. 260/2.5
3,808,018 4/1974 Plueddemann ...................... 106/218
4,342,742 8/1982 Sebag et al. ......................... 424/365

FOREIGN PATENT DOCUMENTS 706907 3/1965 Canada .............................. 260/443
0017122 3/1980 European Pat. Off. .
0017121 8/1980 European Pat. Off. .
2542338 3/1977 Fed. Rep. of Germany ........ 424/70

Primary Examiner—Dale R. Ore
Attorney, Agent, or Firm—Cushman, Darby & Cushman; George A. Grindahl

[57] ABSTRACT

New cationic polydiorganosiloxanes are disclosed that are substantive to proteinaceous substrates. These cationic polydiorganosiloxanes have methyl substituents, and diaminoalkyl substituents reacted with benzyl chloride. These cationic polydiorganosiloxanes are easily emulsified and are useful for treating human hair, human skin, and animal fur.

11 Claims, No Drawings

CATIONIC POLYDIORGANOSILOXANES FOR TREATING PROTEINACEOUS SUBSTRATES

This application is a division, of application Ser. No. 561,404, filed Dec. 14, 1983, now U.S. Pat. No. 4,472,566.

BACKGROUND OF THE INVENTION

The present invention relates to new cationic polydiorganosiloxanes useful in treating proteinaceous substrates. The cationic polydiorganosiloxanes of the present invention are substantive to proteinaceous substrates. By substantive, it is meant herein, having an affinity for a substrate, and being persistently adherent to that substrate through, e.g., subsequent washing cycles.

Cationic silicones derived from aminoalkyl substituted silicones are not unknown. Canadian Pat. No. 706,907, issued Mar. 30, 1965, discloses organosilicon compounds and polymers containing

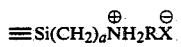

units, wherein X is a halogen atom, R is an alkyl, arylalkyl, or substituted arylalkyl radical, and a has a value of from 3 to 4. Said compounds and polymers are described in the above Canadian Patent as useful antifoams and fiberglass sizing agents.

U.S. Pat. No. 3,278,465, issued Oct. 11, 1966, discloses a method of manufacturing polysiloxanes having, as substituents, a broad variety of polar water-solubilizing radicals, which radicals form salts. Among said radicals are disclosed quaternary ammonium salts formed by reacting a polysiloxane containing monoaminoalkyl substituents with benzyl chloride. Quaternary ammonium salts, as described in U.S. Pat. No. 3,278,465, are salts in which each of the four valences of the positively charged nitrogen atom is satisfied with a monovalent hydrocarbon radical. Said salts are described as useful in stabilizing polyurethane foam.

European Applications for Patent Nos. 17,121, filed Mar. 29, 1979, and 17,122, filed Mar. 29, 1979, disclose cationic polydiorganosiloxanes wherein quaternary ammonium groups are formed by the addition of benzyl chloride to a monoaminoalkyl substituent. Said monoaminoalkyl substituent contains an amide linkage, or an ether linkage. The cationic polydiorganosiloxanes of these European Applications are disclosed as useful hair cosmetics.

U.S. Pat. No. 3,808,018, issued Apr. 30, 1974, discloses a wide variety of silanes which form effective primer compositions when mixed with, or used in conjunction with, organic tackifiers. One of the silanes disclosed is

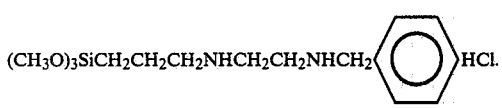

Unfortunately, this silane is not hydrolytically stable, and releases toxic methanol upon its exposure to water, or even upon exposure to ambient atmospheric humidity. This silane cannot be contemplated as a treatment agent for proteinaceous substrates, nor is such a use contemplated in the disclosure of said U.S. Pat. No. 3,808,018.

None of the preceding patent applications or patents address themselves to substantive fluids comprising cationic substituents which are the benzyl chloride salts of diaminoalkyl-substituted polydiorganosiloxanes. The term diaminoalkyl, as referred to herein, means a radical substituent, bonded to a silicon atom, having the formula $-C_mH_{2m}NHC_nH_{2n}NH_2$, wherein m has a value of from 2 to 5 inclusive, and n has a value of from 1 to 5 inclusive.

Specific hair care formulations in which the cationic polydiorganosiloxane of the present invention can be incorporated, as well as a variety of other substantive fluids, are disclosed and claimed in Copending Application Ser. No. 380,178, filed May 20, 1982, and assigned to the assignee of the present application, now abandoned.

BRIEF SUMMARY OF THE INVENTION

The present invention relates to polydiorganosiloxanes having methyl substituents, cationic substituents, and, optionally, hydroxyl end groups. The cationic substituents have the formula

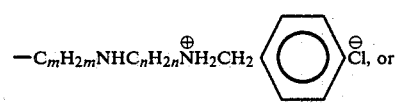

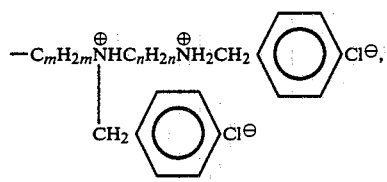

which formulae are further explained below.

It is an object of the present invention to provide new cationic polydiorganosiloxanes. It is a further object to provide polydiorganosiloxanes that are substantive to proteinaceous substrates. It is still a further object to provide a substantive fluid that has good compatibility with water.

These, and other objects will become apparent to those skilled in the art upon consideration of the present disclosure. Said objects are realized by the compositions of the present invention, and the use of said compositions.

The compositions of the present invention are particularly distinguished by their cationic substituents, which are described by the general formula:

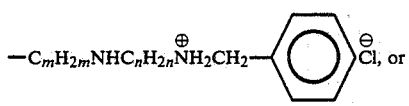

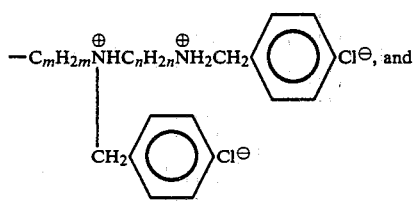

equivalently by the general formula:

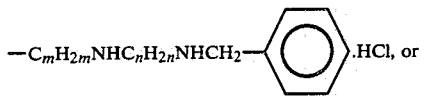, or

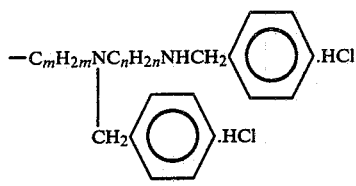

DETAILED DESCRIPTION OF THE INVENTION

The presention invention relates to a cationic polydiorganosiloxane having the general formula $Me_2QSiO(Me_2SiO)_x(MeRSiO)_ySiQMe_2$, wherein Me represents the —$CH_3$ radical, R represents a radical described by the formula

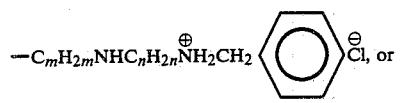

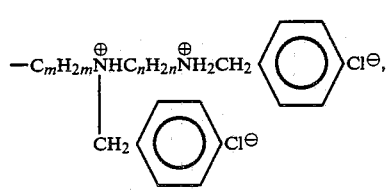

wherein m has a value of from 2 to 5 inclusive, and n has a value of from 1 to 5 inclusive, Q is selected from the group consisting of the R radical, the Me radical and the —OH radical, x has a value of from 5 to 200, and y has a value of from 1 to 30.

The present invention also relates to a method for persistently adhering a polydiorganosiloxane to proteinaceous substrates, said method comprising applying to a proteinaceous substrate selected from the group consisting of human hair, human skin, animal fur and feathers a composition comprising a cationic polydiorganosiloxane having the general formula $Me_2QSiO(Me_2SiO)_x$-$(MeRSiO)_ySiQMe_2$, wherein Me represents the —$CH_3$ radical, R represents a radical described by the formula

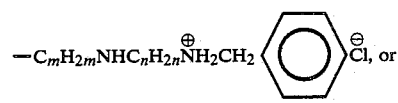, or

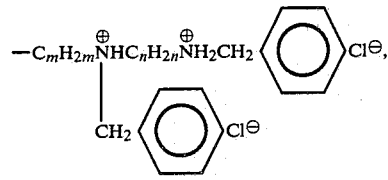

wherein m has a value of from 2 to 5 inclusive, and n has a value of from 1 to 5 inclusive, Q is selected from the group consisting of the R radical, the Me radical, and the —OH radical, x has a value of from 5 to 200, and y has a value of from 1 to 30.

The cationic polydiorganosiloxanes of the present invention are described by the general formula: $Me_2Q$-$SiO(Me_2SiO)_x(MeRSiO)_ySiQMe_2$. Me represents the —$CH_3$ radical and R represents a cationic radical as described by the above general formula, wherein m has a value of from 2 to 5 inclusive, and n has a value of from 1 to 5 inclusive. Q, in the formula for the cationic polydiorganosiloxane of the present invention is selected from R radicals, Me radicals, and hydroxyl radicals; the value of x is from 5 to 200, and the value of y is from 1 to 30.

In the cationic radical, two embodiments are preferred. A first preferred cationic radical is that radical wherein m has a value of 3, and n has a value of 2. A second preferred radical is that radical wherein m has a value of 4 and n has a value of 2.

A specific example of the first preferred cationic radical is

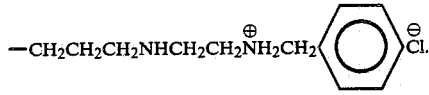

A specific example of the second preferred cationic radical is

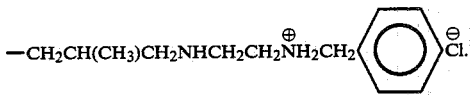

In the above general formula for the cationic polydiorganosiloxane substantive fluids of the present invention, a value of x of from 80 to 200 is preferred, and a value of y of from 1 to 3 is preferred. A preferred Q group for the formula for said fluid is the Me radical.

The compositions of the present invention are preferably made by reacting a polydiorganosiloxane having methyl substituents, diaminoalkyl substituents, and, optionally, hydroxyl end groups, with benzyl chloride. By diaminoalkyl substituents it is meant herein substituents having the formula —$C_mH_{2m}NHC_nH_{2n}NH_2$, wherein m and n have values as hereinabove set forth.

Polydiorganosiloxanes having methyl substituents, hydroxy substituents, and diaminoalkyl substituents as hereinabove described are commercially available. Alternatively, said polydiorganosiloxanes can be synthesized by well-known equilibration procedures, coreacting polydimethylsiloxane having either trimethylsiloxy end groups or dimethyl hydroxy siloxy end groups, with suitable silanes substituted with methyl radicals and diaminoalkyl radicals. U.S. Pat. No. 3,355,424, issued Nov. 28, 1967, is hereby incorporated herein by reference to teach a method of synthesis for polydiorganosiloxanes having methyl substituents, optional hydroxy substituents, and diaminoalkyl substituents.

Benzyl chloride is widely available commercially and the preparation of benzyl chloride need not be further considered herein.

Reaction of the polydiorganosiloxane starting material having methyl substituents, diaminoalkyl substituents, and, optionally hydroxy substituents, with benzyl chloride, is preferably accomplished, in a reaction step, by contacting said polydiorganosiloxane with an amount of benzyl chloride approximately equimolar to the moles of the diaminoalkyl substituent present in said polydiorganosiloxane starting material. That is, about 1 mole of benzyl chloride is added for each mole of $-C_mH_{2m}NHC_nH_{2n}NH_2$ substituent present. More preferably, the polydiorganosiloxane starting material is contacted with an amount of benzyl chloride which is within a range of $\pm 10\%$ the amount equimolar to the moles of diaminoalkyl substituent present.

It is believed that contacting the polydiorganosiloxane starting material with a molar excess of benzyl chloride results in the dibenzylated product, i.e., a substantive fluid where R is

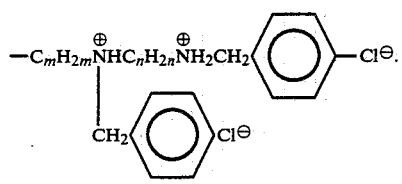

The following model compound experiments show that a molar excess of benzyl chloride can result in the dibenzylated product.

In a first model compound experiment, 10.0 grams of a model compound having the formula Me₃SiOSiMeOSiMe₃
|
CH₂CH(CH₃)CH₂NHCH₂CH₂NH₂ were mixed together with the equimolar quantity, 3.76 g, of

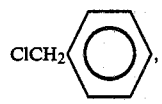

in 10 g of ethanol. This mixture was held at a reflux temperature of 80° C. for a period of three hours. The product was stripped on a thin film rotary evaporator at a temperature of 90° C. and a pressure of 133 Pa.

A viscous clear fluid weighing 13.3 g was recovered. The hydrolyzable chloride test, as hereinbelow described, showed 7.65% Cl, compared to 7.67% theoretical of the monosubstituted product. Additionally, the proton nuclear magnetic resonance spectrum of the product was consistent with the monosubstituted product.

In a second model compound experiment, 5.00 g of the model compound (0.0145 moles), and 3.79 g of

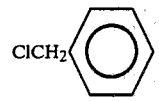

(0.0297 moles) were mixed, reacted in 10 g of ethanol, and stripped by the procedure hereinabove set forth. The product consisted of 7.33 g of a yellow, highly viscous oil. The hydrolyzable chloride test and proton nuclear magnetic resonance tests, hereinafter described, showed 8.93% Cl, and a

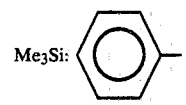

mole ratio of 7/1.4. These test results indicate that some of the disubstituted product was formed.

The reaction to form the cationic polydiorganosiloxane of the present invention is preferably carried out at a temperature of from 20° C. to 100° C. for a period of time of from 1 hour to 24 hours in duration. Progress of the reaction can be monitored viscometrically and/or by analysis of hydrolyzable chloride as hereinafter described.

Preferably, the reaction step delineated above is accomplished with no solvent present in the reaction mixture. However, the reaction step can be accomplished with a suitable solvent present. Examples of suitable solvents include aliphatic hydrocarbon solvents, such as pentane, hexane, and heptane; aromatic hydrocarbon solvents, such as benzene, toluene, and mesitylene; alcohols, such as methanol, ethanol, propanol and the like.

Removing undesired solvent and/or small amounts of unreacted benzyl chloride after the reaction can be accomplished by an optional stripping step, wherein the product of the reaction is exposed to reduced pressure and/or elevated temperature for a period of time sufficient to substantially remove volatile components therefrom. A period of time sufficient to remove said volatile components can be determined by monitoring the concentration of volatile components by, e.g., gas-liquid chromatography. More simply, the stripping step can be continued until the weight of the product of the reaction step comes to a substantially constant value.

The cationic polydiorganosiloxanes of the present invention are advantageously applied to proteinaceous substrates. Proteinaceous substrates to which said cationic polydiorganosiloxanes of the present invention can be applied include, but are not limited to, human hair, human skin, animal fur, feathers, and other proteinaceous substrates.

By animal fur it is meant herein the pelts of fur-bearing animals prepared as articles of apparel or decoration. Examples of fur-bearing animals are rabbits, mink, raccoons, foxes, squirrels, otters, bears, beaver, and the like. Additionally, it is meant herein by animal fur wool and articles of apparel or decoration derived therefrom; further, it is meant herein by animal fur, the coats of pets, such as dogs or cats.

The cationic polydiorganosiloxane of the present invention can be applied to the proteinaceous substrate either dispersed in a suitable solvent, per se or emulsified in water.

Examples of suitable solvents include, but are not limited to, aliphatic hydrocarbon solvents, such as pentane, hexane, heptane, and the like; and aromatic hydrocarbon solvents, such as toluene, mesitylene and the like. Other suitable solvents will be apparent to those skilled in the art.

While the cationic polydiorganosiloxanes of the present invention can be applied to the proteinaceous substrate per se or dispersed in a suitable solvent, it is highly preferred to apply said polydiorganosiloxanes by incorporating said polydiorganosiloxanes in formulated, water-base products, preferably in the form of an emulsion of the cationic polydiorganosiloxane of the present invention in water.

The cationic polydiorganosiloxane of the present invention can be applied to human hair by incorporating said cationic polydiorganosiloxane of the present invention into such formulated products as hair conditioners, shampoos, hair straigtheners, and the like, and applying said formulations to human hair in the normal manner. The cationic polydiorganosiloxane of the present invention can be applied to human skin by incorporating said cationic polydiorganosiloxane of the present invention in formulations such as cleansing creams, cleansing lotions, emollient creams, emollient lotions, hormone creams, hand creams, hand lotions, suntan preparations, foundation make-up, shaving preparations, antiperspirants, deodorants, and the like, and applying the formulation to human skin in the normal manner. The cationic polydiorganosiloxane of the present invention can be applied to animal fur by incorporating said cationic polydiorganosiloxane of the present invention in formulations such as fur dressings, wool conditioners, wool cleaners, dog shampoos and the like, and applying said formulation to animal fur in the normal manner.

The normal manner of applying the above formulations is generally well known. Thus hair conditioners can be massaged, combed, or brushed into hair; shampoos are used in washing hair; skin care formulations as hereinabove set forth are wiped on and/or rubbed on the skin; formulations such as fur dressings are rubbed or sprayed onto the fur; dog shampoos are used in washing dogs; and the like. Those skilled in the art will be aware of these and other modes of application.

Advantageously, the cationic polydiorganosiloxane of the present invention are easily emulsified. Ease of emulsion is clearly desirable when incorporating an ingredient into water-based formulations.

Emulsions can be formed by mixing from 0.1% to about 60% by weight, based on the total weight of the formulation, of the cationic polydiorganosiloxanes of the present invention with 39.9% to 99.9% by weight, based on the total weight of the formulation, of water, and applying to the resultant mixture high shear mixing means, such as a colloid mill or homogenizer. In order to enhance the stability of an emulsion, from 0.1% to 15%, by weight, based on the total weight of the formulation, of one or more surfactants can be added to the above mixture prior to application of the high shear mixing means. The identity of the surfactant is not critical. The type of surfactant used does not appear to be critical as long as the emulsion is homogeneous and uniform in appearance. The surfactant can be anionic, cationic, or nonionic.

Examples of suitable anionic surfactants include sulfonation products of saturated acids and their glycerides, sulfonation products of amides, phosphoric esters of the above-named groups, alkaryl sulfonates and the like.

Examples of suitable cationic surfactants include aliphatic amines, aromatic amines with aliphatic substituents, organic quaternary ammonium compounds, polyethylenediamine, polypropanolpolyethanolamines and the like.

Examples of suitable nonionic surfactants include condensation products of fatty substances with ethylene oxide, condensation products of phenolic compounds having aliphatic side chains with ethylene oxide and the like.

The cationic polydiorganosiloxanes of the present invention combine a highly desirable degree of water compatibility with a high degree of substantivity, which combination renders said cationic polydiorganosiloxanes of the present invention useful in a wide range of formulations for treating proteinaceous substrates.

The following examples are intended to further illustrate, but not limit, the present invention. Parts and percentages herein are by weight unless otherwise specified. Viscosities reported herein were measured in centistokes at 25° C. and the resulting values were converted to m$^2$/second by multiplying said values by $1.000 \times 10^{-6}$ m$^2$/second/centistoke, and rounding the result of said multiplication to three significant figures. Pressures were measured herein in mm Hg, and said measured pressures were converted to Pa by multiplying said measured pressure by $1.33 \times 10^2$ Pa/mm Hg, and rounding the result of said multiplication to two significant figures.

The methyl radical is represented by Me in the following examples.

EXAMPLE 1

In this example, 0.3 g ($2.4 \times 10^{-3}$ moles) of benzyl chloride were mixed with 10.0 g of a polydiorganosiloxane having the average formula $$Me_3SiO(Me_2SiO)_{96}(MeSiO)_2SiMe_3$$
$$|$$
$$(CH_2)_3NH(CH_2)_2NH_2.$$

Said polydiorganosiloxane had a viscosity of $1.5 \times 10^{-4}$ m$^2$/second, and contained approximately $2.6 \times 10^{-3}$ moles of diaminoalkyl substituent. The resulting clear mixture was held at room temperature overnight, after which said mixture was observed to be slightly higher in viscosity than the initial mixture. The reaction product was clear and homogeneous in appearance, and had the approximate structure

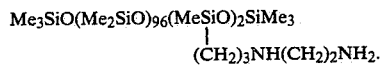

EXAMPLE 2

A cationic polydiorganosiloxane bearing the cationic radical

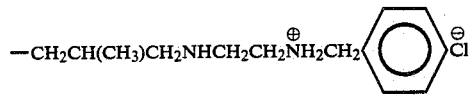

and having the same general formula as the cationic polydiorganosiloxane of Example 1, was prepared by the general procedure of Example 1. Said polydiorganosiloxane was dissolved in D₂O (deuterium oxide) and analyzed by proton (H¹) nuclear magnetic resonance spectroscopy. Proton signals at the following sigma values were correlated with the following molecular segments:

| Sigma Value (ppm) | Group |
| --- | --- |
| 0.8 | SiCH₃ |
| 1.7 | SiCH₂ |
| 2.7 | CH |
| 3.9 | NCH₂ |
| 5.3 | NH |
| 7.6 | 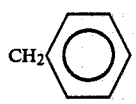 |

The proton ratios agreed in general with the structure presented herein. The spectrum was noted to be unusually broad.

EXAMPLE 3

A mixture consisting of 10.0 g (2.6×10⁻³ moles of diaminoalkyl substituent), of the polydiorganosiloxane starting material of Example 1, and 0.7 g (5.6×10⁻³ moles) of benzyl chloride was prepared and held overnight at room temperature. The subsequent reaction product had a substantially higher viscosity than the initial mixture; said product was clear and homogeneous in appearance, and had the approximate structure:

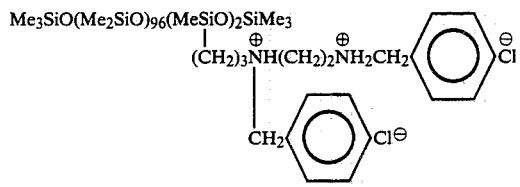

EXAMPLE 4

In this example, a 1 l flask equipped with a mechanical stirrer, a water cooled condenser, a heating mantle, a thermometer, and a temperature regulator, was charged with 500 g (0.13 moles of diaminoalkyl substituent), of the polydiorganosiloxane starting material of Example 1. The flask was also charged with 16.6 g (0.13 moles) of benzyl chloride. The resultant mixture was continuously stirred, and said mixture was heated.

A sample of said mixture was withdrawn, and analyzed for hydrolyzable chloride using the method of Dow Corning Corporate Test Method 0018, in which method the sample to be analyzed was first hydrolyzed with an aqueous solution of sodium methoxide, and the concentration of resulting chloride ion was determined by titration against a standardized silver nitrate solution in the well-known manner. The value for chloride ion thus obtained was converted to moles, and the value in moles was then divided by the total moles of benzyl chloride that had been charged to the flask. The result of this division was multiplied by 100% to generate a percentage conversion for the reaction.

The sampling, hydrolyzing, titrating, and calculating described hereinabove were repeated at various stages of the reaction to generate the data displayed in Table 1.

TABLE 1

| Reaction History of Example 4 | | |
| --- | --- | --- |
| Time (Min.) | Temperature | Theoretical % Conversion |
| 0 | 22° C. | 3.3% |
| 15 | 63° C. | — |
| 18 | 94° C. | — |
| 45 | 95° C. | 13.8% |
| 90 | 92° C. | 79.4% |
| 100 | Heat Turned Off | — |
| Overnight | 25° C. | 93.0% |

The final product, after being held at room temperature overnight, was stripped of volatile materials on a thin film evaporator at a temperature of 100° C. and a pressure of 130 Pa. The volatile material removed in this manner constituted 0.5 g.

After allowing to cool, the product of the above reaction was filtered. Said product was a light yellow fluid having a viscosity of 5.90×10⁻³ m²/second and had an average formula of

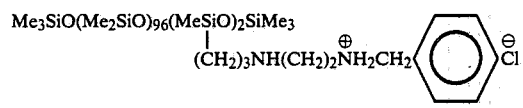

EXAMPLE 5

The general procedure of Example 4 was followed to produce a cationic polydiorganosiloxane of the present invention having the same average formula as that listed for the product of Example 4. The cationic polydiorganosiloxane of the present invention thus produced was incorporated into the following hair conditioning formulation:

Cationic polydiorganosiloxane of this example 35.0 parts

Triton ®X405, octylphenoxypolyethyleneoxide, a nonionic surfactant manufactured by Rohm and Haas Co., Philadelphia, PA: 3.6 parts Tergitol ®TMN-6, trimethylnonylpolyethyleneoxide, a nonionic surfactant manufactured by Union Carbide Co., Dansbury, CT: 3.06 parts Ethylene glycol: 1.0 parts Water: 57.34 parts Total Parts: 100.0 parts The components listed hereinabove were physically mixed, and subsequently exposed to high shear mixing to produce a stable, emulsified hair conditioner. Said hair conditioner has been a stable emulsion for more than one year.

Said hair conditioner was evaluated by first applying said hair conditioner to human hair and observing the relative ease of combing of the hair in the wet state, as well as the feel of the hair in the wet state. Feel and relative ease of combing were also evaluated after the hair had dried. A comb rating was assigned for each determination. Multiple determinations by an experienced observer were performed, and a number from 1 to 5 assigned, wherein 1 indicated maximum ease of combing. Comb ratings from the multiple determinations were averaged, and the results are displayed in Table 2.

The treated hair was then subjected to three shampoo cycles, and the evaluation scheme set forth hereinabove was repeated. See Table 2.

Note that the results for the present example were essentially equivalent before and after the three shampoo cycles, which equivalency indicates a high degree of substantivity.

The polydiorganosiloxane starting material described in Example 1, a known substantive hair conditioning substance, was substituted for the cationic polydiorganosiloxane of the present invention into the hair conditioning formulation listed hereinabove, and the mixture thus resulting was emulsified. The hair conditioning formulation thus derived was tested in parallel with the hair conditioning formulation containing the cationic polydiorganosiloxane of the present invention. See Table 2 for results.

Additionally, untreated hair was tested by the evaluation procedure described hereinabove. See Table 2.

TABLE 2

| | Evaluation as a Hair Conditioner | | |
|---|---|---|---|
| Substantive Fluid: | Polydiorganosiloxane Starting Material Of Example 1 | None | Cationic Polydiorganosiloxane of the Present Invention From Example 1 |
| Hair Type | Virgin Dark | Virgin Dark | Virgin Dark |
| Wet Feel | Slightly Sticky | Rough | Slightly Sticky |
| Wet Comb Rating | 1.0 | 3.5 | 1.2 |
| Dry Comb Rating | 1.1 | 2.0 | 1.0 |
| | Results After Three Shampoos | | |
| Wet Feel | Somewhat Raspy | — | Somewhat Raspy |
| Wet Comb Rating | 1.2 | — | 1.5 |
| Dry Comb Rating | 1.0 | — | 1.0 |

Note that the results using the cationic polydiorganosiloxane of the present invention were essentially equivalent to the results obtained using the known substantive fluid. Additionally the cationic polydiorganosiloxane of the present invention is more water compatible, and was found to be more readily emulsified than the known substantive fluid.

That which is claimed is:

1. A method for persistently adhering a polydiorganosiloxane to proteinaceous substrates, said method comprising applying to a proteinaceous substrate selected from the group consisting of human hair, human skin, animal fur and feathers a composition comprising a cationic polydiorganosiloxane having the general formula $Me_2QSiO(Me_2SiO)_x(MeRSiO)_ySiQMe_2$, wherein Me represents the —$CH_3$ radical, R represents a radical described by the formula

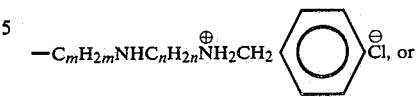

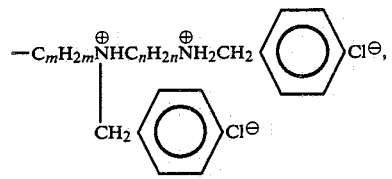

wherein m has a value of from 2 to 5 inclusive, and n has a value of from 1 to 5 inclusive, Q is selected from the group consisting of the R radical, the Me radical, and the —OH radical, x has a value of from 5 to 200, and y has a value of from 1 to 30.

2. The method of claim 1 wherein m has a value of 3 and n has a value of 2.

3. The method of claim 2 wherein R is the

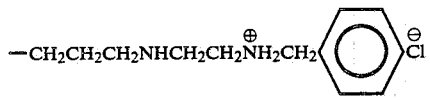

radical.

4. The method of claim 3 wherein x has a value of from 80 to 200, and y has a value of from 1 to 3.

5. The method of claim 4 wherein Q is the —$CH_3$ radical.

6. The method of claim 4 wherein Q is the —OH radical.

7. The method of claim 1 wherein m has a value of 4 and n has a value of 2.

8. The method of claim 7 wherein R is the

radical.

9. The method of claim 8 wherein x has a value of from 80 to 200 and y has a value of from 1 to 3.

10. The method of claim 9 wherein Q is the —$CH_3$ radical.

11. The method of claim 9 wherein Q is the —OH radical.

* * * * *

UNITED STATES PATENT AND TRADEMARK OFFICE
CERTIFICATE OF CORRECTION

PATENT NO. : 4,597,964

DATED : July 1, 1986

INVENTOR(S) : Maris J. Ziemelis and Charles A. Roth

It is certified that error appears in the above-identified patent and that said Letters Patent is hereby corrected as shown below:

On the Cover Page, in the Assignees section, delete "Aplin & Barrett, Ltd., Dorset, England;" so that this section reads --Dow Corning Corporation, Midland, Mich.--.

On the Cover Page, in the Attorney, Agent or Firm section, delete "Cushman, Darby & Cushman" so that this section reads --George A. Grindahl--.

In Col. 7, line 19, "straigtheners" should read --straighteners--.

In Col. 10, line 47, "Dansbury" should read --Danbury--.

Signed and Sealed this

Seventh Day of October, 1986

[SEAL]

Attest:

Attesting Officer

DONALD J. QUIGG

Commissioner of Patents and Trademarks